(12) United States Patent
Ceron et al.

(10) Patent No.: US 7,281,955 B2
(45) Date of Patent: Oct. 16, 2007

(54) SYSTEM OF CONNECTION OF A PROBE TERMINAL TO A CONNECTOR HEAD IN AN IMPLANTABLE MEDICAL DEVICE

(75) Inventors: Claudio Ceron, Castagneto (IT); Guido Gaggini, Milan (IT)

(73) Assignee: Ela Medical S.A.S., Montrouge (FR)

( * ) Notice: Subject to any disclaimer, the term of this patent is extended or adjusted under 35 U.S.C. 154(b) by 0 days.

(21) Appl. No.: 11/259,616

(22) Filed: Oct. 25, 2005

(65) Prior Publication Data

US 2006/0134967 A1    Jun. 22, 2006

(30) Foreign Application Priority Data

Oct. 25, 2004    (FR) .................................. 04 11331

(51) Int. Cl.
*H01R 24/04* (2006.01)

(52) U.S. Cl. ...................................... 439/668

(58) Field of Classification Search .............. 439/668, 439/482, 909, 212; 607/116, 115, 10, 32; 606/637; 428/492
See application file for complete search history.

(56) References Cited

U.S. PATENT DOCUMENTS

RE31,990 E * 9/1985 Sluetz et al. .................. 607/38

4,612,100 A    9/1986    Edeling et al.

FOREIGN PATENT DOCUMENTS

| DE | 3 116 040 | 11/1982 |
|----|-----------|---------|
| FR | 2 654 345 | 5/1991  |
| FR | 2 765 486 | 1/1999  |
| GB | 2 331 998 | 6/1999  |

* cited by examiner

*Primary Examiner*—Alexander Gilman
(74) *Attorney, Agent, or Firm*—Orrick Herrington & Sutcliffe, LLP

(57) ABSTRACT

A system of connection of a probe terminal to a connection head of an implantable medical device. A connection terminal is assembled at the proximal end of a probe to be inserted in a cavity of a connector head of the housing of an implantable medical device. The connection terminal is covered on its external surface by a layer of anti-adhesion material, in particular a carbon film laid down by cathodic sputtering with a thickness less than 1 μm. In the alternative, the layer can be applied on the interior wall of the cavity of the connector head.

12 Claims, 1 Drawing Sheet

FIG_1
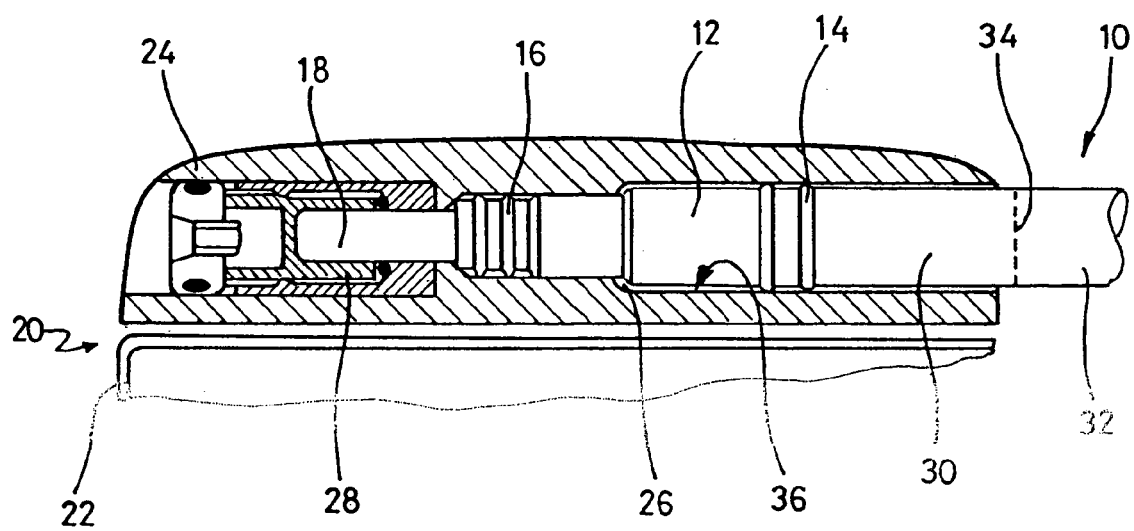

SYSTEM OF CONNECTION OF A PROBE TERMINAL TO A CONNECTOR HEAD IN AN IMPLANTABLE MEDICAL DEVICE

FIELD OF THE INVENTION

The present invention relates to "medical devices," as defined by the Jun. 14, 1993 directive 93/42/CE of the Council of the European Communities. It applies in particular to medical devices such as cardiac prostheses for stimulation, defibrillation, and/or cardioversion. This application is not restrictive, however. The invention generally can be applied to a variety of devices, such as neurological apparatuses, pumps for diffusion of medical substances, cochlear implants, and implanted biological sensors.

BACKGROUND OF THE INVENTION

The above-identified devices generally consist of a system formed by a "generator" containing the active part of the device, and one or more probes mechanically and electrically connected to the generator. More precisely, the generator consists of a case, containing a power supply and the various electronic circuits of the device, and a connector head equipped with one or more female cavities able to receive a connecting terminal located at the proximal end of a probe. The electrical and mechanical connection of the probe to the generator is achieved by insertion of the connecting terminal into the female cavity, which typically is carried out by a surgeon at the time of implantation of the device.

Generators typically have to be replaced after a couple of years because their batteries wear out. The intervention required at that time consists of opening the subcutaneous pocket containing the generator, disconnecting the connecting terminal from the probe (the probe remaining in place), inserting this terminal in the new generator, and then placing the new generator in the pocket, which will be closed again and sutured.

After several years of implantation, it is often difficult to separate the connecting terminal from the generator. Indeed, over the years, the infiltration and deposit of bodily fluids, dead cells, and fibrous tissues tends to create an adhesion of the connecting terminal to the interior surface of the connector head. To overcome this adhesion, the effort exerted on the sheath of the probe to extract the terminal can sometimes cause rupturing of the probe sheath, so that it becomes necessary either to implant a new probe or to cut the end part of the probe and connect a new connecting terminal to it. In either case, this operation is long and must be done carefully, so that, in addition to the increased risk for the patient, the duration and the cost of intervention are increased.

OBJECTS AND SUMMARY OF THE INVENTION

One of the goals of the present invention is to resolve the above-described difficulty by proposing a connector structure that facilitates disconnecting the connection terminal from the connector head, notwithstanding infiltration and deposit of matter on the terminal/connector head interface over the passing of years.

The connection terminal, which can be inserted into a cavity of the connector head of the device to carry out a mechanical and electric connection, is according to the present invention covered on its external surface by a layer of anti-adhesion material. This layer preferably extends primarily over the length of the portion of the terminal located inside the cavity after insertion of the terminal in the connector head. Alternatively, the layer can be coated on the interior wall of the cavity of the connector head.

The layer, which preferably has a uniform thickness lower than 1 µm, is advantageously a carbon film, deposited by cathodic sputtering.

BRIEF DESCRIPTION OF THE DRAWING

One now will describe an embodiment of the invention, by reference to the annexed FIG. 1, which is a cross-section of a connector head with a probe terminal inserted inside.

DETAILED DESCRIPTION OF THE INVENTION

In FIG. 1, reference 10 indicates generally the proximal end of an implantable probe of a device, for example, an endocardiac probe for sensing/stimulation or defibrillation. This probe comprises an insulating sleeve 12, generally made out of silicone material, equipped with annular ridges 14, 16, making it possible to ensure at the same time a precise axial positioning and sealing of the assembly. In the illustrated example, the probe comprises a cylindrical conducting element 18 connected to a probe electrode.

The proximal end of the probe 10 is intended to be connected to a generator 20, of which is shown the upper part of the case 22 and the connector head 24. The connector head 24 comprises a cylindrical cavity 26 having dimensions and form homologous with those of the connection terminal, so as to form a receptacle for the connection terminal. The connector head 24 also comprises an electric connection 28 intended to come into contact with the conducting element 18 to ensure connection of the conducting element to the internal circuits of generator 20.

According to the present invention, the connection terminal is covered on its external surface by a layer of anti-adhesion material, in particular a carbon film laid down by cathodic sputtering. The deposit of this additional layer is carried out on area 30 of the portion of the connection terminal intended to be placed inside cavity 26, while avoiding covering the area 32 that will remain outside the connector head. In other words, a separation 34 between areas 30 and 32 will be located slightly outside the connector head. Thus, the anti-adhesion coating will not bother the surgeon when the surgeon exerts a force on the sheath probe to disconnect the probe from the generator 20. The anti-adhesion film can also be laid down on the surface of the interior wall 36 of cavity 26.

U.S. Pat. Nos. 5,370,684 and 5,387,247, both assigned to Sorin Biomedica SpA, describe the manner of coating by cathodic sputtering a thin film of carbon on an implanted prosthesis. Both of these patents are hereby incorporated by reference in their entirety. The patents illustrate the deposit of a film of carbon on implants such as catheters and cardiac artificial valves made of polyurethane or silicone. However, in the patents, the carbon film is selected for its properties of biocompatibility between the implant and the environment, in order to reduce the risks of rejection or degradation of the prosthesis, in particular on parts in contact with blood flow of the patient.

In the present invention, the carbon film is used because the inventors have appreciated that its properties provide a reduction of adherence between two parts in contact, e.g., the portion of the connection terminal that gets inserted in the connector head. The choice of carbon also has the salutory advantage of an excellent biocompatibility, making it possible to guarantee a high stability of the coating applied to polymeric material, even with a layer of low thickness and even having been in contact with biomaterials over the course of many years.

Due to the presence of this anti-adhesion coating, when the probe has to be withdrawn at the time the generator is changed, even if bodily fluids have penetrated the cavity of the connector, the layer of carbon will have prevented development of an adherence between the connector and the generator head, thus reducing considerably the force necessary to separate these two elements and, consequently, the risk of rupturing the proximal part of the probe.

One skilled in the art will appreciate that the present invention can be practiced by other than the described embodiments, which are presented for purposes of illustration and not of limitation.

We claim:

1. A connection terminal for insertion into a cavity of a connector head of an implantable medical device, said connection terminal having an external surface covered with a layer of an anti-adhesion material that extends primarily over a portion of the terminal located inside said cavity after said connection terminal is inserted in said connector head.

2. The connection terminal of claim 1 wherein said layer of anti-adhesion material has a uniform thickness.

3. The connection terminal of claim 1 wherein said layer comprises a carbon film.

4. The connection terminal of claim 1 wherein said layer is a laid down by cathodic sputtering.

5. The connection terminal of claim 1 wherein said layer has a thickness less than 1 µm.

6. An implantable medical device, comprising a connector head with a cavity able to receive a connection terminal located at a proximal end of a connection probe, said device characterized in that an interior wall of said cavity is covered with a layer of anti-adhesion material.

7. The connection terminal of claim 6, wherein said layer of anti-adhesion material extends primarily over a portion of the terminal located inside said cavity after said connection terminal is inserted in said connector head.

8. The connection terminal of claim 6 wherein said layer of anti-adhesion material has a uniform thickness.

9. The connection terminal of claim 6 wherein said layer comprises a carbon film.

10. The connection terminal of claim 6 wherein said layer is a laid down by cathodic sputtering.

11. The connection terminal of claim 6 wherein said layer has a thickness less than 1 µm.

12. An implantable medical device, comprising a connector head with a cavity able to receive a connection terminal located at a proximal end of a connection probe, said device further characterized in that an interior wall of said cavity is covered with a layer of anti-adhesion material, and an external surface of said connection terminal is covered with a layer of an anti-adhesion material that extends primarily over a portion of the terminal located inside said cavity after said connection terminal is inserted in said connector head.

* * * * *